United States Patent
Lugmair et al.

(10) Patent No.: US 9,815,045 B2
(45) Date of Patent: Nov. 14, 2017

(54) METAL OXIDE CATALYST MATERIAL AND PROCESSES FOR MAKING AND USING SAME

(71) Applicant: CLARIANT CORPORATION, Louisville, KY (US)

(72) Inventors: Claus G. Lugmair, Santa Cruz, CA (US); Hailian Li, Union City, CA (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 15/061,033

(22) Filed: Mar. 4, 2016

(65) Prior Publication Data

US 2016/0279618 A1 Sep. 29, 2016

Related U.S. Application Data

(60) Provisional application No. 62/136,807, filed on Mar. 23, 2015.

(51) Int. Cl.

| | | |
|---|---|---|
| *B01J 37/08* | (2006.01) | |
| *B01J 37/03* | (2006.01) | |
| *C07C 45/35* | (2006.01) | |
| *B01J 23/889* | (2006.01) | |
| *B01J 35/00* | (2006.01) | |
| *B01J 23/00* | (2006.01) | |
| *C07C 253/26* | (2006.01) | |
| *B01J 37/00* | (2006.01) | |
| *B01J 23/887* | (2006.01) | |
| *B01J 35/02* | (2006.01) | |

(52) U.S. Cl.
CPC ......... *B01J 23/8898* (2013.01); *B01J 23/002* (2013.01); *B01J 23/8876* (2013.01); *B01J 35/0013* (2013.01); *B01J 37/0045* (2013.01); *B01J 37/08* (2013.01); *C07C 45/35* (2013.01); *C07C 253/26* (2013.01); *B01J 35/023* (2013.01); *B01J 37/0081* (2013.01); *B01J 37/03* (2013.01); *B01J 2523/00* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,040,978 A | 8/1977 | Li |
| 4,168,246 A | 9/1979 | Tao |
| 4,377,534 A | 3/1983 | Grasselli |
| 4,590,173 A | 5/1986 | Sasaki |
| 4,766,232 A | 8/1988 | Grasselli |
| 4,863,891 A | 9/1989 | Grasselli |
| 5,093,299 A | 3/1992 | Suresh |
| 5,212,137 A | 5/1993 | Suresh |
| 5,223,469 A | 6/1993 | Chen |
| 5,658,842 A | 8/1997 | Midorikawa |
| 5,663,112 A | 9/1997 | Ahn |
| 5,870,664 A | 2/1999 | Sata |
| 6,437,193 B1 | 8/2002 | Contractor |
| 6,462,232 B1 | 10/2002 | Nakamura |
| 7,473,666 B2 | 1/2009 | Yanagi |
| 7,576,232 B2 | 8/2009 | Seely |
| 8,480,998 B2 | 7/2013 | Hagemeyer |
| 2006/0199730 A1 | 9/2006 | Seely |
| 2015/0238939 A1* | 8/2015 | Yoshida ................. C07C 45/35 558/324 |
| 2016/0051967 A1 | 2/2016 | Sokolovskii |

FOREIGN PATENT DOCUMENTS

| | | |
|---|---|---|
| EP | 0253409 | 1/1988 |
| JP | 2009220051 | 10/2009 |
| WO | 199003809 | 1/1999 |

* cited by examiner

*Primary Examiner* — Samantha Shterengarts

(57) ABSTRACT

The present disclosure relates to metal oxide catalyst materials useful, for example, in the ammoxidation of propylene or isobutylene, processes for making them, and processes for making acrylonitrile and methacrylonitrile using such catalyst materials. In certain aspects, a catalyst material is a fused composite of a metal oxide catalyst and nanoparticulate silica, the nanoparticulate silica comprising in the range of about 40 wt % to about 80 wt % of silica having a particle size in the range of 10 nm to 35 nm, and in the range of about 20 wt % to about 60 wt % of silica having a particle size in the range of 36 nm to 80 nm. The metal oxide catalyst can be, for example, a molybdenum-containing mixed metal oxide catalyst.

21 Claims, No Drawings

METAL OXIDE CATALYST MATERIAL AND PROCESSES FOR MAKING AND USING SAME

CROSS-REFERENCE TO RELATED APPLICATIONS

This application claims priority to U.S. Provisional Patent Application Ser. No. 62/136,807 filed Mar. 23, 2015, which is incorporated herein by reference in its entirety.

BACKGROUND OF THE DISCLOSURE

1. Field of the Disclosure

The present disclosure relates generally to catalyst materials and processes for making and using them. More particularly, the present disclosure relates to metal oxide catalyst materials useful, for example, in the ammoxidation of propylene or isobutylene, processes for making them, and processes for making acrylonitrile and methacrylonitrile using such catalysts.

2. Technical Background

Molybdenum-iron-bismuth oxide catalysts have conventionally been used for the reaction of propylene or isobutylene with ammonia and oxygen to make acrylonitrile or methacrylonitrile. Such "ammoxidation" reactions are typically performed at high temperature in the gas phase, often in fluidized bed reactors. The catalyst materials themselves often include a variety of additional elements, such as cerium, cobalt, potassium, cesium, chromium, antimony, as promoters to increase the catalytic efficacy of the catalytic material. The catalyst materials are conventionally made in a batch process by coprecipitation of metal containing precursors such as nitrates with ammonium molybdate, followed by spray-drying of the resulting slurry and calcining of the resulting particles to provide oxide material. More complex multiple-step preparations are also known.

Ammoxidation catalysts are typically made with on the order of 50 wt % silica as a carrier material. Such catalyst materials can be made by coprecipitation in the presence of a silica sol, followed by spray drying and calcining as described above. The silica helps to bind the catalyst material, thus improving attrition resistance (e.g., resistance to breakage due to collisions in a fluidized system). Attrition resistance is a key parameter for catalysts to be used the fluidized bed systems typically used in ammoxidation processes.

There remains a need for improved ammoxidation catalysts that provide not only acceptable attrition resistance, but also desirable activity (e.g., overall reaction of propylene or isobutylene starting material) and desirable selectivity (e.g., fraction of reacted starting material converted to acrylonitrile or methacrylonitrile).

SUMMARY OF THE DISCLOSURE

In one aspect, the present disclosure provides a catalyst material including
 a silica carrier in an amount in the range of about 25 wt % to about 75 wt %, the silica carrier comprising
  in the range of about 40 wt % to about 80 wt % of silica having a particle size in the range of 10 nm to 35 nm (or, in some embodiments, in the range of 20 nm to 35 nm), and
  in the range of about 20 wt % to about 60 wt % of silica having a particle size in the range of 36 nm to 80 nm; and
 a metal oxide catalyst in an amount in the range of about 25 wt % to about 75 wt %.

In another aspect, the present disclosure provides a catalyst material including
 a silica carrier in an amount in the range of about 25 wt % to about 75 wt %, and
 a metal oxide catalyst in an amount in the range of about 25 wt % to about 75 wt %,
the catalyst material being formed as a fused composite of at least the metal oxide and nanoparticulate silica, the nanoparticulate silica comprising
  in the range of about 40 wt % to about 80 wt % of silica having a particle size in the range of 10 nm to 35 nm (or, in some embodiments, in the range of 20 nm to 35 nm), and
  in the range of about 20 wt % to about 60 wt % of silica having a particle size in the range of 36 nm to 80 nm.

In another aspect, the present disclosure provides a process for making a catalyst material, and catalyst materials made by such a process, the catalyst material comprising
 a silica carrier in an amount in the range of about 25 wt % to about 75 wt %, and
 a metal oxide catalyst in an amount in the range of about 25 wt % to about 75 wt %,
the process including
 fusing nanoparticulate silica with the metal oxide catalyst or a precursor thereof, wherein the nanoparticulate silica comprises
  in the range of about 40 wt % to about 80 wt % of silica having a particle size in the range of 10 nm to 35 nm (or, in some embodiments, in the range of 20 nm to 35 nm), and
  in the range of about 20 wt % to about 60 wt % of silica having a particle size in the range of 36 nm to 80 nm.

In various aspects as described herein, the metal oxide catalyst can be, for example, a mixed metal oxide. For example, the metal oxide catalyst can be a molybdenum-containing mixed metal oxide. In certain embodiments, the mixed metal oxide is of the formula $Mo_xBi_yFe_zA_a\Phi_b\Gamma_bD_dE_eO_v$, wherein
 x is in the range of 10 to 14;
 y is in the range of 0.1 to 5;
 z is in the range of 0.5 to 5;
 A is at least one element selected from Ni and Co;
 a is in the range of 1 to 10;
 $\Phi$ is at least one element selected from the lanthanides, Mg, Cr, Mn, Zn and Ca;
 b is in the range of 0.1 to 6;
 $\Gamma$ is at least one element selected from W, Sn, V, Ti, Zr, Ga, Hf, Nb, Ta, In and Al;
 c is in the range of 0 to 8;
 D is at least one element selected from Li, Na, K, Rb and Cs;
 d is in the range of 0.02 to 2;
 E is at least one element selected from any element other than Mo, Bi, Fe, O, and those defined in A, $\Phi$, $\Gamma$ and D;
 e is in the range of 0 to 5; and
 v is the number of oxygen atoms required to satisfy the valence requirements of the other component elements Mo, Bi, Fe, A, $\Phi$, $\Gamma$, and E.

In another aspect, the disclosure provides a process for the conversion of propylene, isobutylene, or a mixture thereof to acrylonitrile, methacrylonitrile, or a mixture thereof, the process including reacting the propylene, isobutylene, or the mixture thereof with ammonia and oxygen in the vapor phase in contact with a catalyst material as described herein.

In another aspect, the disclosure provides a process for the conversion of propylene, isobutylene, or a mixture thereof to acrolein, methacrolein, or a mixture thereof, the process including reacting the propylene, isobutylene, or the mixture thereof with oxygen in the vapor phase in contact with a catalyst material as described herein.

In another aspect, the disclosure provides a mixed metal oxide catalyst having the formula $Mo_{12}Bi_yFe_zCo_aCe_{b1}Mg_{b2}Mn_{b3}Cr_{b4}K_{d1}Cs_{d2}O_y$, in which y is in the range of 0.05 to 0.4, z is in the range of 1 to 2.5, a is in the range of 4.2 to 6.2, b1 is in the range of 0.2 to 0.6, b2 is in the range of 1 to 3, b3 is in the range of 0.1 to 1.0, b4 is in the range of 0.1 to 0.4, d1 is in the range of 0.01 to 0.15, and d2 is in the range of 0.01 to 0.8.

DETAILED DESCRIPTION

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the catalyst material). All mol % values are based on the moles of metal atoms.

As described above, nanoparticulate silica (particulate silica with a very small particle size, often provided as a sol) are typically used to form a silica carrier for ammoxidation catalyst materials, to provide the materials with desirable resistance to attrition. The inventors have noted that use of nanoparticulate silica having an average particle size less than 20 nm can produce highly attrition-resistant catalyst materials. However, such catalyst materials can contain a large fraction of micropores, resulting in high activity accompanied by undesirably low selectivity. The inventors have also noted that use of a nanoparticulate silica with a larger average particle size (e.g., at least about 50 nm average particle size) can result in a catalyst material with relatively larger pores and a higher selectivity for acrylonitrile. But such catalysts materials typically have unacceptably low attrition resistance, making them unsuitable for industrial application in the fluidized bed systems typically used in ammoxidation processes.

The inventors have determined that use of a combination of a nanoparticulate silica having a relatively small average particle size with a nanoparticulate silica having a relatively larger particle size, in certain proportions can provide an ammoxidation catalyst that has good activity and selectivity, while retaining good attrition resistance.

Thus, one aspect of the disclosure is a catalyst material useful, for example, as an ammoxidation catalyst in the synthesis of acrylonitrile or methacrylonitrile. The catalyst material includes a silica carrier in an amount in the range of about 25 wt % to about 75 wt %. The silica carrier comprises in the range of about 40 wt % to about 80 wt % of silica having a particle size in the range of 10 nm to 35 nm (or, in some embodiments, in the range of 20 nm to 35 nm), and in the range of about 20 wt % to about 60 wt % of silica having a particle size in the range of 36 nm to 80 nm. The catalyst material also includes a metal oxide catalyst (for example, a molybdenum-containing mixed metal oxide, e.g., of the formula $Mo_xBi_yFe_zA_a\Phi_b\Gamma_cD_dE_eO_v$ as described herein) in an amount in the range of about 25 wt % to about 75 wt %. As the person of ordinary skill in the art will appreciate, the catalyst material itself will be formed as a fused composite of nanoparticulate silica particles and metal oxide particles.

Another aspect of the disclosure is a catalyst material useful, for example, as an ammoxidation catalyst in the synthesis of acrylonitrile or methacrylonitrile. The catalyst material includes a fused composite of nanoparticulate silica in an amount in the range of about 25 wt % to about 75 wt %, and a metal oxide catalyst (for example, a molybdenum-containing mixed metal oxide, e.g., of the formula $Mo_xBi_yFe_zA_a\Phi_b\Gamma_cD_dE_eO_v$ as described herein) in an amount in the range of about 25 wt % to about 75 wt %. The nanoparticulate silica comprises in the range of about 40 wt % to about 80 wt % of silica having a particle size in the range of 10 nm to 35 nm (or, in some embodiments, in the range of 20 nm to 35 nm), and in the range of about 20 wt % to about 60 wt % of silica having a particle size in the range of 36 nm to 80 nm.

Another aspect of the disclosure provides a catalyst material including a silica carrier in an amount in the range of about 25 wt % to about 75 wt %, and a metal oxide catalyst (for example, a molybdenum-containing mixed metal oxide, e.g., of the formula $Mo_xBi_yFe_zA_a\Phi_b\Gamma_cD_dE_eO_v$ as described herein) in an amount in the range of about 25 wt % to about 75 wt %. The catalyst material is made by a process that includes fusing nanoparticulate silica with the metal oxide catalyst or a precursor thereof. The nanoparticulate silica comprises in the range of about 40 wt % to about 80 wt % of silica having a particle size in the range of 10 nm to 35 nm (or, in some embodiments, in the range of 20 nm to 35 nm), and in the range of about 20 wt % to about 60 wt % of silica having a particle size in the range of 36 nm to 80 nm.

The catalyst material may be provided in any suitable form. In certain embodiments, the catalyst material is provided as a plurality of discrete particles, as is common for catalysts to be used in fluidized bed applications. The discrete particles can be formed in a variety of particle sizes and distributions. For example, in certain embodiments, the discrete particles have an average discrete particle size in the range of about 10 μm to about 200 μm. In various other embodiments, the discrete particles have an average discrete particle size in the range of about 10 μm to about 100 μm, or about 10 μm to about 80 μm, or about 20 μm to about 200 μm, or about 20 μm to about 100 μm, or about 20 μm to about 80 μm, or about 35 μm to about 200 μm, or about 35 μm to about 100 μm, or about 35 μm to about 80 μm.

The discrete particles desirably have a relatively narrow distribution of particle sizes. For example, in various embodiments as described above, at least 90% of the discrete particles are about 10 μm or greater in size, and at least 90% of the discrete particles are about 200 μm or less in size; or at least 90% of the discrete particles are about 10 μm or greater in size, and at least 90% of the discrete particles are about 100 μm or less in size; or at least 90% of the discrete particles are about 10 μm or greater in size, and at least 90% of the discrete particles are about 80 μm or less in size; or at least 90% of the discrete particles are about 20 μm or greater in size, and at least 90% of the discrete particles are about 200 μm or less in size; or at least 90% of the discrete particles are about 20 μm or greater in size, and at least 90% of the discrete particles are about 100 μm or less in size; or at least 70% of the discrete particles are about 20 μm or greater in size, and at least 70% of the discrete particles are about 80 μm or less in size; or at least 70% of the discrete particles are about 35 μm or greater in size, and at least 90% of the discrete particles are about 200 μm or less in size; or at least 70% of the discrete particles are about 35 μm or greater in size, and at least 90% of the discrete particles are about 100 μm or less in size; or at least 70% of the discrete particles are about 35 μm or greater in size, and at least 70% of the discrete particles are about 80 μm or less in size. The discrete particles can be, for example, substantially spheroidal in shape, as would result from a spray drying process. The person of ordinary skill in the art can tune the spray drying process (or other processes) to provide the desired particle shape and size.

Of course, in other embodiments, the catalyst material can be formed in other shapes. For example, the catalyst material can be formed into shapes such as spheres, pellets, cylinders (hollow or otherwise), symmetrical or asymmetrical tri-quadrulobes, for example, using extrusion or tableting methods. Such catalyst materials may be suitable for use in fixed bed reactors. Catalyst materials may also be coated on to a substrate or support, such as a ceramic surface or an internal surface of a reactor.

As described above, the catalyst materials of the disclosure include a silica carrier present in an amount in the range of about 25 wt % to about 75 wt %. In certain embodiments of the catalyst materials as described herein, the silica carrier is present in an amount in the range of about 35 wt % to about 65 wt %, or about 40 wt % to about 60 wt %, or about 45 wt % to about 55 wt %, or about 25 wt % to about 65 wt %, or about 25 wt % to about 55 wt %, or about 35 wt % to about 55 wt %, or about 35 wt % to about 75 wt %, or about 45 wt % to about 75 wt %, or about 45 wt % to about 65 wt %. For example, in certain embodiments, the silica carrier is present in an amount of about 50 wt % of the catalyst material.

As described above, in certain embodiments the silica carrier includes in the range of about 40 wt % to about 80 wt % of silica having a particle size in the range of about 10 nm to about 35 nm (or, in some embodiments, in the range of 20 nm to 35 nm), and in the range of about 20 wt % to about 60 wt % of silica having a particle size in the range of about 36 nm to about 80 nm. Similarly, in certain embodiments the nanoparticulate silica includes in the range of about 40 wt % to about 80 wt % of silica having a particle size in the range of 10 nm to 35 nm (or, in some embodiments, in the range of 20 nm to 35 nm), and in the range of about 20 wt % to about 60 wt % of silica having a particle size in the range of 36 nm to 80 nm. The present inventors have determined that this particular combination of particle sizes and relative amounts (and particular combinations as described herein) can provide catalyst materials that are not only sufficiently resistant to attrition, but also provide desirable activity and acrylonitrile selectivity.

In certain embodiments of the catalyst materials as described herein, the silica carrier or the nanoparticulate silica includes about 40 wt % to about 70 wt %, or about 40 wt % to about 65 wt %, or about 40 wt % to about 60 wt %, or about 50 wt % to about 80 wt %, or about 50 wt % to about 70 wt %, or about 50 wt % to about 60 wt %, or about 55 wt % to about 70 wt %, or about 55 wt % to about 65 wt %, or about 55 wt % to about 60 wt %, or about 60 wt % to about 80 wt %, or about 60 wt % to about 70 wt %, or about 60 wt % to about 65 wt %, or about 57 wt % to about 63 wt % of silica having a particle size in the range of 10 nm to 35 nm. In certain embodiments of the catalyst materials as described herein, the silica having a particle size in the range of 10 nm to 35 nm has an average particle size in the range of about 10 nm to about 30 nm, or about 15 nm to about 25 nm, or about 16 nm to about 30 nm, or about 16 nm to about 25 nm, or about 17 nm to about 23 nm, or about 20 nm to about 30 nm, or about 20 nm to about 25 nm, or about 20 nm to about 23 nm.

In certain embodiments of the catalyst materials as described herein, the silica carrier or the nanoparticulate silica includes about 40 wt % to about 80 wt %, or about 40 wt % to about 70 wt %, or about 40 wt % to about 65 wt %, or about 40 wt % to about 60 wt %, or about 50 wt % to about 80 wt %, or about 50 wt % to about 70 wt %, or about 50 wt % to about 60 wt %, or about 55 wt % to about 70 wt %, or about 55 wt % to about 65 wt %, or about 55 wt % to about 60 wt %, or about 60 wt % to about 80 wt %, or about 60 wt % to about 70 wt %, or about 60 wt % to about 65 wt %, or about 57 wt % to about 63 wt % of silica having a particle size in the range of 10 nm to 30 nm. In certain embodiments of the catalyst materials as described herein, the silica having a particle size in the range of 10 nm to 30 nm has an average particle size in the range of about 10 nm to about 30 nm, or about 15 nm to about 25 nm, or about 16 nm to about 30 nm, or about 16 nm to about 25 nm, or about 17 nm to about 23 nm, or about 20 nm to about 30 nm, or about 20 nm to about 25 nm, or about 20 nm to about 23 nm.

In certain embodiments of the catalyst materials as described herein, the silica carrier or the nanoparticulate silica includes about 40 wt % to about 80 wt %, or about 40 wt % to about 70 wt %, or about 40 wt % to about 65 wt %, or about 40 wt % to about 60 wt %, or about 50 wt % to about 80 wt %, or about 50 wt % to about 70 wt %, or about 50 wt % to about 60 wt %, or about 55 wt % to about 70 wt %, or about 55 wt % to about 65 wt %, or about 55 wt % to about 60 wt %, or about 60 wt % to about 80 wt %, or about 60 wt % to about 70 wt %, or about 60 wt % to about 65 wt %, or about 57 wt % to about 63 wt % of silica having a particle size in the range of 20 nm to 35 nm. In certain embodiments of the catalyst materials as described herein, the silica having a particle size in the range of 20 nm to 35 nm has an average particle size in the range of about 20 nm to about 30 nm, or about 20 nm to about 25 nm, or about 20 nm to about 23 nm.

In certain embodiments of the catalyst materials as described herein, the silica carrier or the nanoparticulate silica includes about 40 wt % to about 80 wt %, or about 40 wt % to about 70 wt %, or about 40 wt % to about 65 wt %, or about 40 wt % to about 60 wt %, or about 50 wt % to about 80 wt %, or about 50 wt % to about 70 wt %, or about 50 wt % to about 60 wt %, or about 55 wt % to about 70 wt %, or about 55 wt % to about 65 wt %, or about 55 wt % to about 60 wt %, or about 60 wt % to about 80 wt %, or about 60 wt % to about 70 wt %, or about 60 wt % to about 65 wt %, or about 57 wt % to about 63 wt % of silica having a particle size in the range of 16 nm to 25 nm. In certain such embodiments, the silica having a particle size in the range of 16 nm to 25 nm has an average particle size in the range of about 16 nm to about 20 nm, or about 17 to about 23 nm, or about 20 nm to about 25 nm.

In certain embodiments of the catalyst materials as described herein, the silica carrier or the nanoparticulate silica includes about 40 wt % to about 80 wt %, or about 40 wt % to about 70 wt %, or about 40 wt % to about 65 wt %, or about 40 wt % to about 60 wt %, or about 50 wt % to about 80 wt %, or about 50 wt % to about 70 wt %, or about 50 wt % to about 60 wt %, or about 55 wt % to about 70 wt %, or about 55 wt % to about 65 wt %, or about 55 wt % to about 60 wt %, or about 60 wt % to about 80 wt %, or about 60 wt % to about 70 wt %, or about 60 wt % to about 65 wt %, or about 57 wt % to about 63 wt % of silica having a particle size in the range of 20 nm to 30 nm. In certain such embodiments, the silica having a particle size in the range of 20 nm to 30 nm has an average particle size in the range of about 20 nm to about 25 nm, or about 25 to about 30 nm, or about 20 nm to about 23 nm.

In certain embodiments of the catalyst materials as described herein, the silica carrier or the nanoparticulate silica includes about 40 wt % to about 80 wt %, or about 40 wt % to about 70 wt %, or about 40 wt % to about 65 wt %, or about 40 wt % to about 60 wt %, or about 50 wt % to about 80 wt %, or about 50 wt % to about 70 wt %, or about 50 wt % to about 60 wt %, or about 55 wt % to about 70 wt %, or about 55 wt % to about 65 wt %, or about 55 wt % to about 60 wt %, or about 60 wt % to about 80 wt %, or about 60 wt % to about 70 wt %, or about 60 wt % to about 65 wt %, or about 57 wt % to about 63 wt % of silica having a particle size in the range of 20 nm to 25 nm. In certain such embodiments, the silica having a particle size in the range of 20 nm to 25 nm has an average particle size in the range of about 20 nm to about 23 nm.

In certain embodiments of the catalyst materials as described herein, the silica carrier or the nanoparticulate silica includes about 20 wt % to about 50 wt %, or about 20 wt % to about 45 wt %, or about 20 wt % to about 40 wt %, or about 30 wt % to about 60 wt %, or about 30 wt % to about 50 wt %, or about 30 wt % to about 45 wt %, or about 30 wt % to about 40 wt %, or about 35 wt % to about 60 wt %, or about 35 wt % to about 50 wt %, or about 35 wt % to about 45 wt %, or about 35 wt % to about 40 wt %, or about 37 wt % to about 43 wt % of the silica having a particle size in the range of 36 nm to 80 nm. In certain embodiments of the catalyst materials as described herein, the silica having a particle size in the range of 36 nm to 80 nm has an average particle size in the range of about 40 nm to about 60 nm, or about 45 nm to about 55 nm, or about 40 nm to about 80 nm, or about 50 nm to about 70 nm.

In certain embodiments of the catalyst materials as described herein, the silica carrier or the nanoparticulate silica includes about 20 wt % to about 50 wt %, or about 20 wt % to about 45 wt %, or about 20 wt % to about 40 wt %, or about 30 wt % to about 60 wt %, or about 30 wt % to about 50 wt %, or about 30 wt % to about 45 wt %, or about 30 wt % to about 40 wt %, or about 35 wt % to about 60 wt %, or about 35 wt % to about 50 wt %, or about 35 wt % to about 45 wt %, or about 35 wt % to about 40 wt %, or about 37 wt % to about 43 wt % of silica having a particle size in the range of 40 nm to 70 nm. In certain such embodiments, the silica having a particle size in the range of 40 nm to 70 nm has an average particle size in the range of about 45 nm to about 65 nm, or about 47 nm to about 53 nm, or about 50 nm to about 60 nm, or about 45 nm to about 50 nm.

In certain embodiments of the catalyst materials as described herein, the silica carrier or the nanoparticulate silica includes about 20 wt % to about 50 wt %, or about 20 wt % to about 45 wt %, or about 20 wt % to about 40 wt %, or about 30 wt % to about 60 wt %, or about 30 wt % to about 50 wt %, or about 30 wt % to about 45 wt %, or about 30 wt % to about 40 wt %, or about 35 wt % to about 60 wt %, or about 35 wt % to about 50 wt %, or about 35 wt % to about 45 wt %, or about 35 wt % to about 40 wt %, or about 37 wt % to about 43 wt % of silica having a particle size in the range of 45 nm to 60 nm. In certain such embodiments, the silica having a particle size in the range of 45 nm to 60 nm has an average particle size in the range of about 45 nm to about 55 nm, or about 47 nm to about 53 nm, or about 50 nm to about 60 nm.

The person of ordinary skill in the art will appreciate that in addition to the silica carrier nanoparticulate silica of the particle sizes described above, the catalyst material may include minor amounts of silica of other particle sizes. But in certain embodiments of the catalyst materials as described herein, at least about 80 wt %, at least about 90 wt %, at least about 95 wt %, at least about 98 wt %, or at least about 99 wt % of the silica carrier is silica having a particle size in the range of about 10 nm to about 80 nm. In one particular embodiment, the silica carrier or nanoparticulate silica consists essentially of silica having a particle size in the range of about 10 nm to about 80 nm.

The particle sizes of the silica carrier or the nanoparticulate silica advantageously form a multimodal distribution (e.g., bimodal), with a first mode having a particle size in the range of 10 nm to 35 nm (or 10 nm to 30 nm, or 20 nm to 35 nm, or 16 nm to 25 nm, or 20 nm to 30 nm, or 20 nm to 25 nm) and a second mode having a particle size in the range of 36 to 80 nm (or 40 nm to 70 nm, or 45 nm to 60 nm).

As described above, the catalyst materials of the disclosure include a metal oxide catalyst in an amount in the range of about 25 wt % to about 75 wt %. For example, in certain embodiments, the metal oxide catalyst is present in an amount in the range of about 30 wt % to about 70 wt %. In other embodiments, the metal oxide catalyst is present in an amount in the range of about 35 wt % to about 65 wt %, or about 40 wt % to about 60 wt %, or about 45 wt % to about 55 wt %, or about 25 wt % to about 65 wt %, or about 25 wt % to about 55 wt %, or about 35 wt % to about 55 wt %, or about 35 wt % to about 75 wt %, or about 45 wt % to about 75 wt %, or about 45 wt % to about 65 wt %. For example, in certain embodiments, the metal oxide catalyst is present in an amount of about 50 wt % of the catalyst material.

The catalyst material can in some embodiments include other materials. However, in certain particularly advantageous embodiments, the silica carrier and the metal oxide are together present in the catalyst material in an amount of at least about 80 wt %, or at least about 90 wt %, or at least about 95 wt %, or at least about 98 wt %, or at least about 99 wt %, or at least about 99.5 wt %, or even at least about 99.9 wt %. For example, in certain embodiments, the catalyst material consists essentially of the silica carrier and the metal oxide.

A number of metal oxide catalysts can be used. For example, in certain embodiments, the metal oxide catalyst is a mixed metal oxide catalyst, for example, a mixed metal oxide ammoxidation catalyst suitable for the conversion of propylene to acrylonitrile and/or isobutylene to methacrylonitrile, and/or for the for the conversion of propylene to acrolein and/or isobutylene to methacrolein. The mixed metal oxide catalyst can, for example, be a molybdenum-containing mixed metal oxide.

As described above, the catalyst materials of the disclosure can in certain embodiments include as the metal oxide catalyst a mixed metal oxide of the formula $Mo_xBi_yFe_zA_a\Phi_b\Gamma_cD_dE_eO_v$, in an amount in the range of about 25 wt % to about 75 wt %. In such embodiments x is in the range of 10 to 14; y is in the range of 0.1 to 5; z is in the range of 0.5 to 5; A is at least one element selected from Ni and Co; a is in the range of 1 to 10; $\Phi$ is at least one element selected from the lanthanides, Mg, Cr, Mn, Zn and Ca; b is in the range of 0.1 to 6; $\Gamma$ is at least one element selected from W, Sn, V, Ti, Zr, Ga, Hf, Nb, Ta, In and Al; c is in the range of 0 to 8; D is at least one element selected from Li, Na, K, Rb and Cs; d is in the range of 0.02 to 2; E is at least one element selected from any element other than Mo, Bi, Fe, O, and those defined in A, $\Phi$, $\Gamma$ and D; e is in the range of 0 to 5; and v is the number of oxygen atoms required to satisfy the valence requirements of the other component elements Mo, Bi, Fe, A, $\Phi$, $\Gamma$, and E. The person of ordinary skill in the art will appreciate that the formulae described herein merely refer to the relative amounts of the various constituents. For example, a material having the formula $Mo_6BiFeA_{0.5}\Phi_{0.5}D_{0.5}O_{2v}$ would also be understood to have the formula $Mo_{12}Bi_2Fe_2A\Phi DO_v$. The stoichiometry of the mixed metal oxide is determined on a dry basis, i.e., discounting any adsorbed water.

As the person of ordinary skill in the art will appreciate, the metal oxide catalyst may be provided in many forms and morphologies. It may include crystalline regions, amorphous regions, or a combination of the two. Moreover, the metal oxide need not be substantially homogeneous; there may be regions of the metal oxide that have varying compositions as compared to the rest of the metal oxide. As the person of ordinary skill in the art will appreciate, the disclosed formula $Mo_xBi_yFe_zA_a\Phi_b\Gamma_cD_dE_eO_v$ (or any other formula disclosed herein) represents the average composition of the metal oxide.

As described above, the coefficient x in the formula $Mo_xBi_yFe_zA_a\Phi_b\Gamma_cD_dE_eO_v$ in the catalyst materials of the disclosure is in the range of 10-14. For example, in various particular embodiments of the catalyst materials as described herein, x is in the range of 11-13. In certain embodiments, x is 12.

As described above, the coefficient y in the formula $Mo_xBi_yFe_zA_a\Phi_b\Gamma_cD_dE_eO_v$ is in the range of 0.1 to 5. For example, in various particular embodiments of the catalyst materials as described herein, y is in the range of 0.1 to 3, or 0.1 to 2, or 0.1 to 1, or 0.1 to 0.5, or 0.1 to 0.35, or 0.15 to 3, or 0.15 to 2, or 0.15 to 1, or 0.15 to 0.5, or 0.15 to 0.35, or 0.2 to 3, or 0.2 to 2, or 0.2 to 1, or 0.2 to 0.5, or 0.2 to 0.35.

As described above, the coefficient z in the formula $Mo_xBi_yFe_zA_a\Phi_b\Gamma_cD_dE_eO_v$ is in the range of 0.5 to 5. For example, in various particular embodiments of the catalyst materials as described herein, z is in the range of 0.5 to 4, or 0.5 to 3, or 0.5 to 2, or 1 to 5, or 1 to 4, or 1 to 3, or 1 to 2, or 1.5 to 5, or 1.5 to 4, or 1.5 to 3, or 1.5 to 2.

As described above, A in the formula $Mo_xBi_yFe_zA_a\Phi_b\Gamma_cD_dE_eO_v$ is at least one element selected from Ni and Co. For example, in various particular embodiments of the catalyst materials as described herein, A is Ni. In other embodiments, A is Co. In still other embodiments, A is a combination of Ni and Co.

As described above, the coefficient a in the formula $Mo_xBi_yFe_zA_a\Phi_b\Gamma_cD_dE_eO_v$ is in the range of 1 to 10. For example, in various particular embodiments of the catalyst materials as described herein, a is in the range of 1 to 8, or 1 to 6.5, or 2 to 10, or 2 to 8, or 2 to 6.5, or 3.5 to 10, or 3.5 to 8, or 3.5 to 6.5, or 4.5 to 10, or 4.5 to 8, or 4.5 to 6.5.

As described above, $\Phi$ in the formula $Mo_xBi_yFe_zA_a\Phi_b\Gamma_cD_dE_eO_v$ is at least one element selected from the lanthanides, Mg, Cr, Mn, Zn and Ca. For example, in various particular embodiments of the catalyst materials as described herein, $\Phi$ is at least one element selected from Ce, Mg, Cr, Mn, Zn and Ca. In other embodiments, $\Phi$ is at least one element selected from Ce, Mg, Cr and Mn. For example, $\Phi$ can include each of Ce, Mg, Cr and Mn.

As described above, the coefficient b in the formula $Mo_xBi_yFe_zA_a\Phi_b\Gamma_cD_dE_eO_v$ is in the range of 0.1 to 6 For example, in various particular embodiments of the catalyst materials as described herein, b is in the range of 0.1 to 5, or 0.1 to 4, or 0.1 to 3.5, or 0.5 to 6, or 0.5 to 5, or 0.5 to 4, or 0.5 to 3.5, or 1 to 6, or 1 to 5, or 1 to 4, or 1 to 3.5, or 2 to 6, or 2 to 5, or 2 to 4, or 2 to 3.5, or 3 to 6, or 3 to 5, or 3 to 4, or 3 to 3.5.

As described above, $\Gamma$ is at least one element selected from W, Sn, V, Ti, Zr, Ga, Hf, Nb, Ta, In and Al. In certain embodiments, $\Gamma$ is at least one element selected from W, Sn, V, Ti and Zr. In other embodiments, $\Gamma$ is at least one element selected from W, Sn and V. In one embodiment, $\Gamma$ is W.

As described above, c is in the range of 0 to 8. In certain embodiments, the mixed metal oxide is substantially free of W, Sn, V, Ti, Zr, Ga, Hf, Nb, Ta, In and Al. Accordingly, in certain embodiments, c is substantially zero. In other embodiments, c is in the range of 0 to 6, or 0 to 4, or 0 to 2, or 0 to 1, or 0 to 0.5, or 0 to 0.2, or 0 to 0.1, or 0.05 to 8, or 0.05 to 6, or 0.05 to 4, or 0.05 to 2, or 0.05 to 1, or 0.05 to 0.5, or 0.05 to 0.2, or 0.05 to 0.1, or 0.1 to 8, or 0.1 to 6, or 0.1 to 4, or 0.1 to 2, or 0.1 to 1, or 0.1 to 0.5, or 0.1 to 0.2.

As described above, D is at least one element selected from Li, Na, K, Rb and Cs. For example, in various particular embodiments of the catalyst materials as described herein, D is at least one element selected from Li, Na, K and Cs. In one embodiment, D is at least one element selected from Li, K and Cs, or selected from K and Cs. In certain embodiments, D is a combination of K and Cs.

As described above, d is in the range of 0.02 to 2. For example, in various particular embodiments of the catalyst materials as described herein, d is in the range of 0.02 to 1, or 0.02 to 0.5, or 0.02 to 0.2, or 0.05 to 2, or 0.05 to 1, or 0.05 to 0.5, or 0.05 to 0.2, or 0.1 to 2, or 0.1 to 1, or 0.1 to 0.5, or 0.1 to 0.2.

As described above, E is at least one element selected from any element other than Mo, Bi, Fe, O, and those defined in A, $\Phi$, $\Gamma$ and D. In certain embodiments, E includes at least one, or includes only transition elements. In certain embodiments, E includes at least one, or includes only elements from Groups IIIA, IVA, VA or VIA. In certain embodiments, E does not include hydrogen or any atoms from Group VIIIA. In certain embodiments, E does not include any actinides or any transuranium elements. In certain embodiments, E includes at least one, or includes only elements selected from Te, Sb, P, Ge and B. In certain embodiments, E includes at least one, or includes only elements selected from Sb and P.

As described above, e is in the range of 0 to 5. In certain embodiments, the mixed metal oxide consists essentially of Mo, Bi, Fe, A, Φ, Γ, E and O. Accordingly, in certain embodiments, e is substantially zero. In other embodiments, e is in the range of 0 to 4, or 0 to 2, or 0 to 1, 0 to 0.5, or 0 to 0.2, or 0 to 0.1, or 0 to 0.05, or 0 to 0.02, or 0 to 0.01, or 0.01 to 5, or 0.01 to 4, or 0.01 to 2, or 0.01 to 1, or 0.01 to 0.5, or 0.01 to 0.2, or 0.01 to 0.1, or 0.01 to 0.05, or 0.01 to 0.02, or 0.05 to 5, or 0.05 to 4, or 0.05 to 2, or 0.05 to 1, or 0.05 to 0.5, or 0.05 to 0.2, or 0.05 to 0.1.

As described above, v is the number of oxygen atoms required to satisfy the valence requirements of the other component elements Mo, Bi, Fe, A, Φ, Γ, and E. The person of ordinary skill in the art will appreciate that the value of y will vary depending on the identities and oxidation states of the various component elements Mo, Bi, Fe, A, Φ, Γ, and E.

The person of ordinary skill in the art will select suitable identities of the metal oxide catalyst (e.g., of the component elements Mo, Bi, Fe, A, Φ, Γ, and E and values of the various coefficients of the metal oxide) based on the state of the art (e.g., the ammoxidation catalyst art), for example, as described in any of U.S. Pat. Nos. 4,766,232, 4,377,534, 4,040,978, 4,168,246, 4,863,891, 5,093,299, 5,12,137, 5,223,469, 5,658,842, 5,663,112, 5,870,664, 7,473,666 and 7,576,232, and International Patent Application Publication no. WO 2014/169163, each of which is hereby incorporated herein by reference in its entirety.

For example, in certain embodiments, the metal oxide catalyst has the formula $Mo_{12}Bi_yFe_zCo_aCe_{b1}Mg_{b2}Mn_{b3}Cr_{b4}K_{d1}Cs_{d2}O_y$, in which y the range of 0.05 to 0.4, z is in the range of 1 to 2.5, a is in the range of 4.2 to 6.2, b1 is in the range of 0.2 to 0.6, b2 is in the range of 1 to 3, b3 is in the range of 0.1 to 1.0, b4 is in the range of 0.1 to 0.4, d1 is in the range of 0.01 to 0.15, and d2 is in the range of 0.01 to 0.8.

Indeed, another aspect of the disclosure is a mixed metal oxide catalyst material having the formula $Mo_{12}Bi_yFe_zCo_aCe_{b1}Mg_{b2}Mn_{b3}Cr_{b4}K_{d1}Cs_{d2}O_y$, in which y is in the range of 0.05 to 0.4, z is in the range of 1 to 2.5, a is in the range of 4.2 to 6.2, b1 is in the range of 0.2 to 0.6, b2 is in the range of 1 to 3, b3 is in the range of 0.1 to 1.0, b4 is in the range of 0.1 to 0.4, d1 is in the range of 0.01 to 0.15, and d2 is in the range of 0.01 to 0.8. The mixed metal oxide can be supported, for example, on an chemically inert carrier, such as, for example, silicon carbide, silicon dioxide, zirconium dioxide, titanium dioxide, aluminum oxides, porous ceramics, sheet silicates, bentonites and mixtures thereof. Such a catalyst material can include, for example, in the range of about 25 wt % to about 75 wt % of the carrier, and in the range of about 25 wt % to about 75 wt % mixed metal oxide.

The catalyst materials described herein can be provided with a variety of different pore volumes, depending, e.g., on the processes used for making them and the desired end use. For example, in certain embodiments, a catalyst material as described herein has a pore volume of about 0.05 to about 1 $cm^3/g$, or about 0.1 to about 1 $cm^3/g$, or about 0.2 to about 1 $cm^3/g$, or about 0.3 to about 1 $cm^3/g$, or about 0.5 to about 1 $cm^3/g$, or 0.05 to about 0.5 $cm^3/g$, or about 0.1 to about 0.5 $cm^3/g$, or about 0.2 to about 0.5 $cm^3/g$. The person of ordinary skill in the art can, in view of the processes described herein, provide a desired pore volume to a catalyst material. Pore volumes are measured by Hg porisometry, and provide the total volume or pores below 5000 Å in size.

The person of ordinary skill in the art can, in view of the processes described herein, provide a desired pore volume to a catalyst material.

Similarly, the catalyst materials described herein can be provided with a variety of different surface areas, depending, e.g., on the processes used for making them and the desired end use. The surface areas are measured using the Brunauer-Emmett-Teller (BET) Surface Area method. In certain embodiments, a catalyst material as described herein has a surface area of about 5 $m^2/g$ to about 150 $m^2/g$, or about 5 $m^2/g$ to about 100 $m^2/g$, or about 5 $m^2/g$ to about 75 $m^2/g$, or about 5 $m^2/g$ to about 50 $m^2/g$, or about 10 $m^2/g$ to about 150 $m^2/g$, or about 10 $m^2/g$ to about 100 $m^2/g$, or about 10 $m^2/g$ to about 75 $m^2/g$, or about 10 $m^2/g$ to about 50 $m^2/g$, or about 20 $m^2/g$ to about 150 $m^2/g$, or about 20 $m^2/g$ to about 100 $m^2/g$, or about 20 $m^2/g$ to about 75 $m^2/g$. In one embodiment, a catalyst material as described herein has a surface area of about 20 $m^2/g$ to about 50 $m^2/g$. The person of ordinary skill in the art can, in view of the processes described herein, provide a desired surface area to a catalyst material.

The catalyst material may be prepared by conventional procedures, as would be understood by the person of ordinary skill in the art. For example, in one embodiment, precipitation techniques are used to make the catalyst material. For example, in one embodiment, the metal oxide is formed by precipitation of one or more water soluble precursor materials with a precipitation agent, for example, in the presence of the nanoparticulate silica. Each precursor material may be a water soluble metal salt such as, but not limited to, a metal nitrate, a metal sulfate, a metal halide, or a metal acetate; certain precursor materials may be provided with the metal species in the anion (e.g. oxide anions of molybdenum, manganese, chromium, tungsten or vanadium). The precipitation agent may be, for example, ammonium hydroxide, ammonium carbonate, a metal hydroxide, or a metal carbonate. Alternatively, the precipitation agent can be a salt of an oxide anion of one of the metal components of the metal oxide, e.g., ammonium paramolybdate. The person of ordinary skill in the art can select other suitable precipitation agents, based on the particular metal oxide precursors and the pH-dependence of their solubility properties. Precipitated materials can be spray-dried to form particles (e.g., substantially spheroid particles), or formed into desired shapes using extrusion and/or tableting methods, as would be evident to the person of ordinary skill in the art. The person of ordinary skill in the art will also appreciate that such materials can be formed with or without a binder, depending on the particular metals used and the desired active material properties. The particles or shapes so formed can be dried and calcined to provide the catalyst materials described herein.

As described above, the use of nanoparticulate silica of two different particle sizes can provide catalyst materials with an improved set of properties. Accordingly, another embodiment of the disclosure provides a process for making a catalyst material as described herein. The process includes fusing nanoparticulate silica with the metal oxide or a precursor thereof, wherein the nanoparticulate silica comprises in the range of about 30 wt % to about 80 wt % of silica having a particle size in the range of 10 nm to 30 nm (or any of the other amounts and ranges described above with respect to the smaller particle size silica), and in the range of about 20 wt % to about 80 wt % of silica having a particle size in the range of 36 nm to 80 nm (or any of the other amounts and ranges described above with respect to the larger particle size silica). As the person of ordinary skill in the art will appreciate, the various relative amounts and proportions of components described above with respect to the catalyst materials can be used in the corresponding processes described herein. As used herein, a metal oxide precursor is a metal-containing salt that can be converted to the corresponding metal oxide by calcining Fusion of the silica carrier and the metal oxide can also occur during the calcining step. Accordingly, to make the catalyst materials described herein, metal oxide precursors can be combined with nanoparticulate silica (e.g., by coprecipitation) to form a slurry, which is then formed (e.g., by spray drying into discrete particles, or by extrusion into a desired shape) and calcined to convert the precursors to the metal oxide and to fuse the metal oxide with the silica carrier.

The metal oxide or the precursor thereof can be provided, for example, by precipitation as described above. Thus, in one embodiment, a process includes precipitating a plurality of metal oxides or precursors thereof in the presence of nanoparticulate silica that includes in the range of about 30 wt % to about 80 wt % of silica having a particle size in the range of 10 nm to 30 nm (or any of the other amounts and ranges described above with respect to the smaller particle size silica), and in the range of about 20 wt % to about 70 wt % of silica having a particle size in the range of 36 nm to 80 nm (or any of the other amounts and ranges described above with respect to the larger particle size silica) to form a solid; and drying (e.g., by spray drying) and calcining the solid to fuse the metal oxide or precursor thereof to the nanoparticulate silica, thereby forming the catalyst materials described herein.

As noted above, the catalyst materials described herein can be used in the conversion of propylene to acrylonitrile, or isobutylene to methacrylonitrile via ammoxidation. Accordingly, various embodiments of the disclosure provide processes for the conversion of propylene, isobutylene, or a mixture thereof to acrylonitrile, methacrylonitrile, or a mixture thereof, the process including reacting the propylene, isobutylene, or the mixture thereof with ammonia and oxygen in the vapor phase with a catalyst material as described herein. In certain embodiments, the process is performed in a fluid bed reactor, although as the person of ordinary skill in the art will appreciate, other types of reactors can be suitably used.

As noted above, the catalyst materials described herein can be also be used in the conversion of propylene to acrolein, or isobutylene to methacrolein via partial oxidation. Accordingly, various embodiments of the disclosure provide processes for the conversion of propylene, isobutylene, or a mixture thereof to acrolein, methacrolein, or a mixture thereof, the process including reacting the propylene, isobutylene, or the mixture thereof with oxygen in the vapor phase with a catalyst material as described herein. In certain embodiments, the process is performed in a fluid bed reactor, although as the person of ordinary skill in the art will appreciate, other types of reactors can be suitably used.

Conditions for the ammoxidation of propylene to acrylonitrile, or of isobutylene to methacrylonitrile, are well-known in the art. For example, U.S. Pat. Nos. 4,766,232, 4,377,534, 4,040,978, 4,168,246, 4,863,891, 5,093,299, 5,212,137, 5,223,469, 5,658,842, 5,663,112, 5,870,664, 7,473,666 and 7,576,232, each of which is hereby incorporated herein by reference in its entirety, describe a variety of ammoxidation processes.

In certain embodiments, the propylene and/or isobutylene is reacted with ammonia and oxygen in contact with a catalyst material as described herein in a fluid bed at an elevated temperature to produce the acrylonitrile and/or methacrylonitrile. As the person or ordinary skill in the art would appreciate, any convenient source of oxygen may be used; for economic considerations, air is a suitable oxygen-providing gas. The reaction can be carried out, for example, at a temperature in the range of about 260° C. to about 600° C., e.g., 310° C. to 500° C., or 350° C. to 480° C., for a variety of contact times, e.g., in the range of 0.1 to 50 seconds, or about 1 to 15 seconds. The molar ratio of oxygen to propylene/isobutylene in the feed can vary; in certain embodiments, the ratio is in the range of 0.5:1 to 4:1, e.g., 1:1 to 3:1. Similarly, the molar ratio of ammonia to olefin in the feed can vary, e.g., from 0.5:1 to 2:1.

Reaction products may be isolated and purified using conventional methodologies. For example, in one embodiment, the reactor effluent is scrubbed with water or an appropriate solvent to remove the reaction products, which are then purified by distillation. It can also be desirable to isolate and purify certain reaction by-products, such as acetonitrile and HCN; the person of ordinary skill can use conventional methodologies to do so.

As noted above, the catalyst materials described herein can be also be used in the conversion of propylene to acrolein, or isobutylene to methacrolein via partial. Accordingly, various embodiments of the disclosure provide processes for the conversion of propylene, isobutylene, or a mixture thereof to acrolein, methacrolein, or a mixture thereof, the process including reacting the propylene, isobutylene, or the mixture thereof with oxygen in the vapor phase with a catalyst material as described herein. In certain embodiments, the process is performed in a fluid bed reactor, although as the person of ordinary skill in the art will appreciate, other types of reactors can be suitably used.

Conditions for the partial oxidation of propylene to acrolein, or of isobutylene to methacrolein, are well-known in the art. For example, U.S. Pat. Nos. 6,437,193, 6,462,232 and 8,480,998, International patent Application Publication no. WO 1999/003809 and European Patent Application Publication no. EP 0253409, each of which is hereby incorporated herein by reference in its entirety, describe a variety of oxidation processes.

In certain embodiments, the propylene and/or isobutylene is reacted with oxygen (e.g., in the presence of nitrogen) in contact with a catalyst material as described herein at an elevated temperature to produce the acrylonitrile and/or methacrylonitrile. As the person or ordinary skill in the art would appreciate, any convenient source of oxygen may be used; for economic considerations, air is a suitable oxygen-providing gas. The reaction can be carried out, for example, at a temperature in the range of about 250° C. to about 600° C., e.g., 310° C. to 500° C., or 350° C. to 480° C., for a variety of contact times, e.g., in the range of 0.1 to 50 seconds, or about 1 to 15 seconds. The molar ratio of oxygen to propylene/isobutylene in the feed can vary, and can be selected by the person of ordinary skill in the art to provide the desired products. In certain embodiments, the acrolein and/or methacrolein can be further reacted (e.g., in a separate process, but without purification) to provide acrylic acid and/or methacrylic acid.

Certain aspects of the disclosure are now explained further via the following non-limiting examples.

EXAMPLES

Comparative Example 1: Single-Silica Catalyst Material Prepared with 20 nm Silica A mixed metal nitrate solution was prepared by mixing 3.328 mL of concentrated $HNO_3$ (70 wt %) with 1.589 mL of a Bi(NO$_3$)$_3$ solution (1.00 M Bi, with 2.0 M HNO$_3$); 1.589 mL of a Ce(NO$_3$)$_3$ solution (2.00 M); 5.949 mL of a Fe(NO$_3$)$_3$ solution (2.404 M); 0.794 mL of a Cr(NO$_3$)$_3$ solution (2.00 M); 5.54 mL of a Mg(NO$_3$)$_2$ solution (3.00 M); 10.40 mL of a Co(NO$_3$)$_2$ solution (4.00 M); 1.871 mL of a Mn(NO$_3$)$_2$ solution (2.00 M, with 0.10 M HNO$_3$); 0.371 mL of a KNO$_3$ solution (1.50 M), and 0.318 mL of a CsNO$_3$ solution (1.00 M). The mixed metal nitrate solution thus obtained was added to a diluted colloidal silica prepared with 38.46 mL of NexSil 20NH4 ammonia-stabilized colloidal silica (40 wt % SiO$_2$, 20 nm average particle size) and 16.67 mL of deionized water with stirring. To the thus-obtained mixture was added a solution of 16.832 g of ammonium paramolybdate [(NH$_4$)$_6$Mo$_7$O$_{24}$·4H$_2$O] in 34.0 mL of deionized water with vigorous stirring to produce a slurry. The resulting slurry was stirred for 1 h, then wet milled for 1 h in a 500 mL bottle containing about 170 mL of zirconia beads (13×13 mm). The milled slurry was aged overnight and then spray dried at an inlet temperature of 194° C. and an outlet temperature of 90° C. The spray dried particles have an average particle size of about 60 □m. The dried catalyst precursor was subjected to calcination in a tube furnace with temperature profile of a ramp to 400° C. at 1° C./min, hold for 2 h, and then followed by another ramp to 590° C. at 3.2° C./min and hold for another 2 h. The airflow rate was controlled at 1 L/min. The final catalyst had the formula: Mo$_{12}$Bi$_{0.2}$Ce$_{0.4}$F$_{1.8}$Cr$_{0.2}$Mg$_{2.094}$Co$_{5.235}$Mn$_{0.471}$K$_{0.07}$C$_{0.04}$O$_x$, with 50 wt % SiO$_2$. A 30 g portion of the catalyst material thus obtained was evaluated in a micro fluid bed reactor with a feed ratio of C$_3$H$_6$/O$_2$/NH$_3$ equal to 1.00/2.25/1.30. The catalyst material exhibited 81.2% acrylonitrile selectivity at 98.8% conversion at wwh (weight of feed/weight of catalyst material/hour)=0.014 h$^{-1}$ and 420° C.

Comparative Example 2: Single Silica Catalyst Material Prepared with 50 nm Silica This catalyst material was prepared in the same manner as Comparative Example 1, except that NexSil 85NH4 ammonia-stabilized colloidal silica (40 wt % SiO$_2$, 50 nm average particle size) was used as the binder instead of NexSil 20NH4. A 30 g portion of the catalyst material thus obtained was evaluated in a micro fluid bed reactor with a feed ratio of C$_3$H$_6$/O$_2$/NH$_3$ equal to 1.00/2.25/1.30. The catalyst material exhibited 79.4% acrylonitrile selectivity at 90.4% conversion at wwh=0.14 h$^{-1}$ and 420° C.

Comparative Example 3: Single Silica Catalyst Prepared with 2 nm Silica

This catalyst material was prepared in the same manner as Comparative Example 1 except that Ludox AS-40 colloidal silica (40 wt % SiO$_2$, 22 nm particle size) was used as the binder instead of NexSil 20NH4. A 30 g portion of the catalyst material thus obtained was evaluated in micro fluid bed reactor with a feed ratio of C$_3$H$_6$/O$_2$/NH$_3$ equal to 1.00/2.25/1.30. The catalyst material exhibited 80.1% acrylonitrile selectivity at 98.5% conversion at wwh=0.14 h$^{-1}$ and 420° C.

Example 1: Mixed Silica Catalyst Prepared with a Mixture of 2 nm Silica and 50 nm Silica A mixed metal nitrate solution was prepared by mixing 6.657 mL of concentrated HNO$_3$ (70 wt %) with 3.178 mL of a Bi(NO$_3$)$_3$ solution (1.00 M, with 2.0 M HNO$_3$); 3.178 mL of a Ce(NO$_3$)$_3$ solution (2.00 M); 11.90 mL of a Fe(NO$_3$)$_3$ solution (2.404 M); 1.589 mL of a Cr(NO$_3$)$_3$ solution (2.00 M); 11.09 mL of a Mg(NO$_3$)$_2$ solution (3.00 M); 20.80 mL of a Co(NO$_3$)$_2$ solution (4.00 M); 3.742 mL of a Mn(NO$_3$)$_2$ solution (2.00 M, with 0.10 M HNO$_3$); 0.742 mL of a KNO$_3$ solution (1.50 M), and 0.636 mL of a CsNO$_3$ solution (1.00 M). The mixed metal nitrate solution thus obtained was added to a diluted colloidal silica prepared with 60.0 g of NexSil 20NH4, 40.0 g of NexSil 85NH4 and 33.33 mL of deionized water with stirring. To the thus-obtained mixture was added a solution of 33.663 g of ammonium paramolybdate [(NH$_4$)$_6$Mo$_7$O$_{24}$·4H$_2$O] in 67.9 mL of deionized water with vigorous stirring to produce a slurry. The resulting slurry was stirred for 1 h, then wet milled for 1 h in a 500 mL bottle containing about 170 mL of zirconia beads (13×13 mm). The milled slurry was aged overnight and then spray dried at an inlet temperature of 194° C. and an outlet temperature of 90° C. The spray dried particles have an average particle size of about 60 □m. The dried catalyst precursor was subjected to a calcination treatment in a tube furnace with a temperature profile of a ramp to 400° C. at 1° C./min, hold for 2 h, and then followed by another ramp to 590° C. at 3.2° C./min and hold for another 2 h. The airflow rate was controlled at 1 L/min. A 30 g sample of the catalyst material thus obtained was evaluated in micro fluid bed reactor with a feed ratio of C$_3$H$_6$/O$_2$NH$_3$ equal to 1.00/2.25/1.30. The catalyst material exhibited 83.4% acrylonitrile selectivity at 97.7% conversion at wwh=0.14 h$^{-1}$ and 420° C.

We claim:
1. A catalyst material for the oxidation or ammoxidation of propylene or isopropylene, the catalyst material comprising a fused composite of
 a silica carrier in an amount in the range of about 25 wt % to about 75 wt %, wherein at least about 80 wt % of the silica carrier is silica having a particle size in the range of 10 nm to 80 nm, and
 a metal oxide catalyst in an amount in the range of about 25 wt % to about 75 wt %, the metal oxide catalyst having the formula Mo$_x$Bi$_y$Fe$_z$A$_a$φ$_b$Γ$_c$D$_d$E$_e$O$_v$, wherein
 x is in the range of 10 to 14;
 y is in the range of 0.1 to 5;
 z is in the range of 0.5 to 5;
 A is at least one element selected from Ni and Co;
 a is in the range of 1 to 10;
 φ is at least one element selected from the lanthanides, Mg, Cr, Mn, Zn and Ca;
 b is in the range of 0.1 to 6;
 Γ is at least one element selected from W, Sn, V, Ti, Zr, Ga, Hf, Nb, Ta, In and Al;
 c is in the range of 0 to 8;
 D is at least one element selected from Li, Na, K, Rb and Cs;
 d is in the range of 0.02 to 2;
 E is at least one element selected from any element other than Mo, Bi, Fe, O, and those defined in A, φ, Γ and D;
 e is in the range of 0 to 5; and
 v is the number of oxygen atoms required to satisfy the valence requirements of the other component elements Mo, Bi, Fe, A, φ, Γ, and E,
the catalyst material being made by a process comprising fusing nanoparticulate silica with the metal oxide catalyst or a precursor thereof,
 wherein the nanoparticulate silica comprises in the range of about 40 wt % to about 80 wt % of silica having a particle size in the range of 10 nm to 35 nm, and in the range of about 20 wt % to about 60 wt % of silica having a particle size in the range of 36 nm to 80 nm.

2. The catalyst material according to claim 1, wherein the silica carrier or the nanoparticulate silica comprises about 50 wt % to about 70 wt % of the silica having a particle size in the range of 10 nm to 35 nm.

3. The catalyst material according to claim 1 about 50 wt % to about 70 wt % of silica having a particle size in the range of 20 nm to 25 nm.

4. The catalyst material according to claim 1 wherein the silica carrier comprises about 30 wt % to about 40 wt % of the silica having a particle size in the range of 36 nm to 80 nm.

5. The catalyst material according to claim 1, wherein the silica carrier or the nanoparticulate silica includes about 30 wt % to about 40 wt % of silica having a particle size in the range of 40 nm to 70 nm.

6. The catalyst material according to claim 1, wherein at least about 90 wt % of the silica carrier is silica having a particle size in the range of 10 nm to 80 nm.

7. The catalyst material according to claim 1, wherein the silica carrier and the metal oxide are together present in the catalyst material in an amount of at least about 95 wt %.

8. The catalyst material according to claim 1, wherein
x is 12;
y is in the range of 0.1 to 1;
z is in the range of 1 to 2.5;
a is in the range of 2 to 8;
b is in the range of 1 to 6;
c is in the range of 0 to 4;
d is in the range of 0.02 to 1; and
e is in the range of 0 to 1.

9. The catalyst material according to claim 1, wherein A is Ni, or A is Co, or A is a combination of Ni and Co.

10. The catalyst material according to claim 1, wherein $\phi$ is at least one element selected from Ce, Mg, Cr, Mn, Zn and Ca.

11. The catalyst material according to claim 1, wherein D is at least one element selected from Li, Na, K and Cs.

12. The catalyst material according to claim 1, wherein E includes at least one element from Groups IIIA, IVA, VA or VIA.

13. The catalyst material according to claim 1, wherein E includes at least one element selected from Te, Sb, P, Ge and B.

14. The catalyst material according to claim 1, wherein the metal oxide catalyst has the $Mo_{12}Bi_yFe_zCo_aCe_{b1}Mg_{b2}Mn_{b3}Cr_{b4}K_{d1}Cs_{d2}O_v$, in which y is in the range of 0.05 to 0.4, z is in the range of 1 to 2.5, a is in the range of 4.2 to 6.2, b1 is in the range of 0.2 to 0.6, b2 is in the range of 1 to 3, b3 is in the range of 0.1 to 1.0, b4 is in the range of 0.1 to 0.4, d1 is in the range of 0.01 to 0.15, and d2 is in the range of 0.01 to 0.8.

15. The catalyst material according to claim 1, formed as a plurality of discrete particles, the discrete particles having an average discrete particle size in the range of about 10 μm to about 200 μm.

16. A process for making a catalyst material according to claim 1, the process comprising
fusing nanoparticulate silica with the metal oxide catalyst or a precursor thereof,
wherein the nanoparticulate silica comprises
in the range of about 40 wt % to about 80 wt % of silica having a particle size in the range of 10 nm to 35 nm, and
in the range of about 20 wt % to about 60 wt % of silica having a particle size in the range of 36 nm to 80 nm,
wherein at least about 80 wt % of the nanoparticulate silica has a particle size in the range of 10 nm to 80 nm.

17. A catalyst material comprising
a silica carrier in an amount in the range of about 25 wt % to about 75 wt %, the silica carrier comprising
in the range of about 40 wt % to about 80 wt % of silica having a particle size in the range of 10 nm to 35 nm, and
in the range of about 20 wt % to about 60 wt % of silica having a particle size in the range of 36 nm to 80 nm,
wherein at least about 80 wt % of the silica carrier is silica having a particle size in the range of 10 nm to 80 nm; and
a metal oxide catalyst in an amount in the range of about 25 wt % to about 75 wt %, the metal oxide catalyst having the formula $Mo_xBi_yFe_zA_a\phi_b\Gamma_cD_dE_eO_v$, wherein
x is in the range of 10 to 14;
y is in the range of 0.1 to 5;
z is in the range of 0.5 to 5;
A is at least one element selected from Ni and Co;
a is in the range of 1 to 10;
$\phi$ is at least one element selected from the lanthanides, Mg, Cr, Mn, Zn and Ca;
b is in the range of 0.1 to 6;
$\Gamma$ is at least one element selected from W, Sn, V, Ti, Zr, Ga, Hf, Nb, Ta, In and Al;
c is in the range of 0 to 8;
D is at least one element selected from Li, Na, K, Rb and Cs;
d is in the range of 0.02 to 2;
E is at least one element selected from any element other than Mo, Bi, Fe, O, and those defined in A, $\phi$, $\Gamma$ and D;
e is in the range of 0 to 5; and
v is the number of oxygen atoms required to satisfy the valence requirements of the other component elements Mo, Bi, Fe, A, $\phi$, $\Gamma$, and E.

18. A catalyst material comprising
a silica carrier in an amount in the range of about 25 wt % to about 75 wt %, and
a metal oxide catalyst in an amount in the range of about 25 wt % to about 75 wt %, the metal oxide catalyst having the formula $Mo_xBi_yFe_zA_a\phi_b\Gamma_cD_dE_eO_v$, wherein
x is in the range of 10 to 14;
y is in the range of 0.1 to 5;
z is in the range of 0.5 to 5;
A is at least one element selected from Ni and Co;
a is in the range of 1 to 10;
$\phi$ is at least one element selected from the lanthanides, Mg, Cr, Mn, Zn and Ca;
b is in the range of 0.1 to 6;
$\Gamma$ is at least one element selected from W, Sn, V, Ti, Zr, Ga, Hf, Nb, Ta, In and Al;
c is in the range of 0 to 8;
D is at least one element selected from Li, Na, K, Rb and Cs;
d is in the range of 0.02 to 2;
E is at least one element selected from any element other than Mo, Bi, Fe, O, and those defined in A, $\phi$, $\Gamma$ and D;

e is in the range of 0 to 5; and v is the number of oxygen atoms required to satisfy the valence requirements of the other component elements Mo, Bi, Fe, A, φ, Γ, and E, the catalyst material being formed as a fused composite of at least the metal oxide catalyst and nanoparticulate silica, the nanoparticulate silica comprising in the range of about 40 wt % to about 80 wt % of silica having a particle size in the range of 10 nm to 35 nm, and in the range of about 20 wt % to about 60 wt % of silica having a particle size in the range of 36 nm to 80 nm, wherein at least about 80 wt % of the nanoparticulate silica has a particle size in the range of 10 nm to 80 nm.

19. A process for making a catalyst material according to claim 18, the process comprising fusing nanoparticulate silica with the metal oxide catalyst or a precursor thereof, wherein the nanoparticulate silica comprises in the range of about 40 wt % to about 80 wt % of silica having a particle size in the range of 10 nm to 35 nm, and in the range of about 20 wt % to about 60 wt % of silica having a particle size in the range of 36 nm to 80 nm, wherein at least about 80 wt % of the nanoparticulate silica has a particle size in the range of 10 nm to 80 nm.

20. A process for the conversion of propylene, isobutylene, or a mixture thereof to acrylonitrile, methacrylonitrile, or a mixture thereof, the process comprising reacting the propylene, isobutylene, or the mixture thereof with ammonia and oxygen in the vapor phase in contact with a catalyst material according to claim 1.

21. A process for the conversion of propylene, isobutylene, or a mixture thereof to acrolein, methacrolein, or a mixture thereof, the process comprising reacting the propylene, isobutylene, or the mixture thereof with oxygen in the vapor phase in contact with a catalyst material according to claim 1.

\* \* \* \* \*